United States Patent [19]

Neumann et al.

[11] 4,153,810

[45] May 8, 1979

[54] PROCESS FOR THE PREPARATION OF ALKYL ETHERS

[75] Inventors: Rainer Neumann, Krefeld; Hans-Helmut Schwarz, Krefeld-Traar; Karl-Heinz Arnold, Cologne, all of Fed. Rep. of Germany

[73] Assignee: Haarmann & Reimer GmbH, Holzminden, Fed. Rep. of Germany

[21] Appl. No.: 852,754

[22] Filed: Nov. 18, 1977

[30] Foreign Application Priority Data

Dec. 9, 1976 [DE] Fed. Rep. of Germany ....... 2655826

[51] Int. Cl.$^2$ .............................................. C07C 41/10
[52] U.S. Cl. .................................. 568/630; 568/632; 568/650; 568/656; 568/658
[58] Field of Search ...................... 260/612 D, 613 D

[56] References Cited

U.S. PATENT DOCUMENTS 3,584,058  6/1971  Hahn ............................... 260/612 D

FOREIGN PATENT DOCUMENTS 197613  7/1967  U.S.S.R. ............................... 260/612 D

*Primary Examiner*—Bernard Helfin
*Attorney, Agent, or Firm*—Sprung, Felfe, Horn, Lynch & Kramer

[57] ABSTRACT

Process for the preparation of alkyl aryl ethers by reacting aromatic hydroxy compounds with aliphatic alcohols in the presence of strongly acidic cation exchangers based on synthetic resins using the aromatic hydroxy compound in excess of the aliphatic alcohol.

6 Claims, No Drawings

PROCESS FOR THE PREPARATION OF ALKYL ETHERS

The invention relates to a process for the preparation of alkyl aryl ethers by reacting aromatic hydroxy compounds with aliphatic alcohols in the presence of cation exchangers.

Processes for the preparation of alkyl aryl ethers are known. In general, these ethers are prepared from salts of aromatic hydroxy compounds and alkyl halides or alkyl sulphates (see, for example, Houben-Weyl, Methoden der organischen Chemie (Methods of Organic Chemistry), volume VI/3, 54 (1965)). This method of preparation does however have the disadvantage that, in addition to the ethers, equivalent amounts of inorganic salts form, which cause considerable pollution of the effluent and also frequently have corrosive action. Thus processes have been developed for the preparation of alkyl aryl ethers by reacting aromatic hydroxy compounds directly with lower aliphatic alcohols. These reactions are conducted for example in the presence of metal oxides and/or metal salts (see Japanese patent applications No. 8099-129 and 71-11494). These processes, which are conducted in the presence of metal oxides and/or metal salts, do however have the disadvantage that during them considerable amounts of nuclear-alkylated compounds form as secondary products (see Japanese patent application No. 8099-129).

Aromatic hydroxy compounds have also been etherified with aliphatic alcohols in the presence of acid ion exchangers, e.g. m-cresol with methanol in the presence of acid ion exchangers at temperatures of 150° C. to 180° C. In this reaction as well considerable amounts of nuclear-alkylated products arise; in addition, because of the high reaction temperature, the life of the ion exchangers is only limited, which in particular makes industrial application difficult (Nippon Kaishi, 8, 1513 (1974)). The reaction of phenol and o-cresol with methanol in the presence of acid ion exchangers is also described in the USSR Patent Specification No. 197,613. In this process methanol is reacted with phenol or o-cresol under pressure in a molar ratio of 1–4:1. The disadvantage of this process is that apart from nuclear-alkylated compounds being formed as secondary product considerable amounts of dimethyl ether arise.

It has now surprisingly been found that the disadvantages of the known processes, in particular the formation of secondary products, are avoided if, in the alkylation of the aromatic hydroxy compounds with aliphatic alcohols in the presence of acid ion exchangers, the aromatic hydroxy compounds are employed in excess of the alcohols. By means of the method according to the invention of using the aromatic hydroxy compounds in excess amounts, the formation of nuclear-alkylated phenols is practically completely prevented. A further substantial advantage is that in the alkylation of polyphenols such as catechol, hydroquinone, etc. essentially only monoalkylation products are obtained. This selective etherification of only one hydroxyl group in polyphenols was not possible by the etherification processes known up until now.

The invention thus relates to a process for the preparation of alkyl aryl ethers by reacting aromatic hydroxy compounds with aliphatic alcohols in the presence of strongly acidic cation exchangers based on synthetic resins, characterised in that at least 3 moles of the aromatic hydroxy compound are used per mol of the aliphatic alcohol.

It has proven particularly advantageous to use a molar ratio of 3–5:1 of aromatic hydroxy compound: aliphatic alcohol.

As examples of the aromatic hydroxy compounds to be alkylated according to the invention there should be mentioned phenol, phenols substituted by $C_1$–$C_4$ alkyl group - such as m-, o- and p-cresol, xylenols and tert.-butylphenol, phenols substituted by halogen atoms, such as m-, o- and p-chlorophenol and 2,4-dichlorophenol, as well as polyphenols such as catechol, resorcinol, hydroquinone and 1,2,4-trihydroxybenzene, also $\alpha$- and $\beta$-naphthol and hydroxyanthracene.

The aliphatic alcohols used as alkylation agents in the process according to the invention are preferably monohydric alcohols containing 1 to 8 carbon atoms, especially 1 to 4 carbon atoms, such as methanol, ethanol, propanol, butanol, isobutanol, pentanol, isopentanol, hexanol, isohexanol, heptanol, isoheptanol, octanol and isooctanol. Preferably methanol and ethanol are used.

In the process according to the invention all strongly acidic cation exchangers based on synthetic resins can in principle be employed. Such strongly acidic cation exchangers are described for example in Kirk-Othmer, Encyclopedia of Chemical Technology, 2nd edition, vol. 11, pp. 871 et seq. The strongly acidic cation exchangers based on polystyrene sulphonic acid cross-linked with divinyl benzene, especially polystyrene sulphonic acids cross-linked with 2 to 4% by weight of divinylbenzene, have however proven especially advantageous. Particularly high space-time yields are achieved with these gel-type strongly acidic cation exchangers of a particular degree of cross-linkage.

The cation exchangers are employed in their $H^+$-form in the process according to the invention. The ion exchangers are preferably employed in the form of commercially available bead polymers, granules or also in powder form.

The quantity of the ion exchangers can vary within wide limits when conducting the process according to the invention. In general the strongly acidic cation exchanger is employed in quantities of 0.5–50% by weight, preferably 1–25% by weight, based on the weight of the starting compounds.

In the process according to the invention it can be advantageous to employ a solvent, if higher melting aromatic hydroxy compounds are used. Organic liquids which can be considered for use as solvents are those in which the starting compound concerned readily dissolves and which are not modified under the reaction conditions. Examples of solvents which may be mentioned are hydrocarbons such as benzene, halogen hydrocarbons, such as chlorobenzene, carbon tetrachloride, 1,2-dichloroethane and chloroform or ethers, such as diethyl ether. The quantities in which the solvents are employed can vary within wide limits. In general only the quantity necessary to dissolve the starting material is added, however, when conducting the reaction in a continuous manner it can be advantageous for technical reasons concerning conveyance to add substantially more solvent.

The process according to the invention is for example carried out by initially introducing the mixture of aliphatic alcohol and hydroxy compound to be etherified, the latter being present in an excess amount, and then adding the acid ion exchanger and heating the mixture to temperatures of 50°–150° C., preferably 110°–130° C.

The process according to the invention can be conducted particularly advantageously in a continuous procedure. A preferred embodiment of the continuous procedure is to carry out the reaction with a fixed catalyst bed. In this case the starting compounds are passed over the ion exchanger, located in a fixed bed, in a continuous stream either individually or after prior mixing.

The process according to the invention can be carried out under reduced, normal or excess pressure. However, in order to achieve high reaction rates and good space-time yields it can be advantageous to carry out the process under increased pressure. This applies, above all, when low-boiling, aliphatic alcohols which are gaseous at the reaction temperature are employed. In this case pressures which are above the autogenous vapour pressure of the reaction mixture are appropriate.

After the alkylation has taken place the resultant reaction mixture can be worked up as follows: first of all, if the process has not been carried out in a fixed bed, the cation exchanger is removed according to customary methods of solid/liquid separation, such as filtering, centrifuging, sedimenting or decanting. The catalyst can be re-used for the alkylation. The alcohol, the water and if appropriate the solvent are first of all separated off from the liquid phase by distillation. The residue then remaining contains the resulting alkyl aryl ether, which can be isolated by methods which are in themselves known, for example distillation or crystallisation.

The alkyl aryl ethers which can be prepared according to the process of the invention are, as is known, intermediate products for the preparation of pesticides, dyes, auxiliary products for plastics, scents, antioxidants and preservatives.

The parts mentioned in the following Examples refer, if not otherwise stated, to parts by weight.

EXAMPLE 1

500 parts of a dry, strongly acidic cation exchanger (polystyrene sulphonic acid cross-linked with 4% by weight divinyl benzene) are arranged in a fixed bed in a vertical tube (inner diameter: 40 mm; capacity: 2 l) and are swollen with phenol to constant volume. The reactor is provided at its lower end with a feed tube, through which the reaction solution can be metered under a counterpressure which compensates the pressure loss in the column. The overflow at the upper end of the reactor is connected to a cooling trap for the purpose of freezing out non-condensed gaseous constituents.

The solution, heated to 100° C., of 470 parts of phenol and 32 parts of methanol (molar ratio 5:1) flows through the fixed bed from the bottom upwards. The average residence time of the liquid phase, based on the empty tube, is 30 hours. By external heating a temperature of 120° C. is set up inside of the reactor.

The resulting reaction mixture consists of 413 parts of phenol, 12 parts of methanol, 66 parts of anisole and 11 parts of water; i.e. the yield of anisole based on reacted methanol (or phenol) is 100%. Secondary products such as nuclear-methylated phenol or anisole or dimethyl ether cannot be detected.

If the alkylation is conducted at 100° C. instead of at 120° C. the yield of anisole is also 100%, based on the reacted methanol (or phenol). Only the rate of the reaction and thus the conversion rate per unit of time is approx. 30% lower.

EXAMPLE 2

470 parts of phenol, 46 parts of ethanol and 103 parts (20% by weight) of the strongly acidic, dry cation exchanger described in Example 1 are stirred for 20 hours at 110° C. in a three-necked flask provided with a stirrer, a reflux cooler and a thermometer.

The resulting reaction mixture consists of: 414 parts of phenol, 73 parts of phenyl ethyl ether, 18 parts of ethanol and 11 parts of water; i.e. the yield of phenetole is approx. 100%, based on reacted ethanol (or phenol). The proportion of nuclear-alkylated compounds is below 1% by weight.

EXAMPLE 3

470 parts of phenol, 74 parts of isobutanol and 109 parts (20% by weight) of the strongly acidic, dry cation exchanger described in Example 1 are reacted under the reaction conditions described in Example 2.

The resulting reaction mixture consists of: 404 parts of phenol, 105 parts of phenyl isobutyl ether, 22.5 parts of isobutanol and 12.5 parts of water; i.e. the yield of phenyl isobutyl ether is 100%, based on reacted isobutanol (or phenol). The proportion of nuclear-alkylated compounds is below 0.2% by weight.

EXAMPLE 4

540 parts of p-cresol, 32 parts of methanol and 114 parts (20% by weight) of the strongly acidic, dry cation exchanger described in Example 1 are reacted under the reaction conditions described in Example 2.

The resulting reaction mixture consists of: 497.9 parts of p-cresol, 47.6 parts of p-methyl anisole, 19.5 parts of methanol and 7 parts of water; i.e. the yield of 4-methylphenyl methyl ether is 100%, based on the reacted methanol (or p-cresol). The proportion of nuclear-alkylated compounds is below 0.3% by weight.

EXAMPLE 5

643 parts of p-chlorophenol, 32 parts of methanol and 67 parts (10% by weight) of the strongly acidic, dry cation exchanger described in Example 1 are reacted for 30 hours under the conditions described in Example 2.

The resulting reaction mixture consists of 553.7 parts of p-chlorophenol, 100.1 parts of p-chloroanisole, 9.6 parts of methanol and 12.6 parts of water; i.e. the yield of 4-chlorophenyl methyl ether is 100% based on the reacted methanol (or p-chlorophenol). The proportion of nuclear-alkylated compounds is below 1% by weight.

EXAMPLE 6

550 parts of catechol, 32 parts of methanol and 116 parts (20% by weight) of the strongly acidic, dry cation exchanger described in Example 1 are reacted under the conditions described in Example 2.

The resulting mixture consists of: 445.5 parts of catechol, 177.8 parts of catechol monomethyl ether, 1.6 parts of methanol and 17.1 parts of water; i.e. the yield of catechol monomethyl ether is approx. 100%, based on the reacted methanol (or catechol). The proportion of nuclear-alkylated compounds is below 0.1% by weight, the proportion of catechol dimethyl ether is below 0.2% by weight.

EXAMPLE 7

720 parts of α-naphthol, 32 parts of methanol and 52 parts (7% by weight) of the strongly acidic dry cation exchanger described in Example 1 are reacted for 60 hours under the reaction conditions described in Example 2.

The resulting reaction mixture consists of: 578.9 parts of α-naphthol, 155 parts of α-naphthyl methyl ether, 0.6 parts of methanol and 17.6 parts of water; i.e. the yield of α-naphthyl methyl ether is 100%, based on the reacted methanol (orα-naphthol). The proportion of nuclear-alkylated compounds is below 0.1% by weight.

EXAMPLE 8

470 parts of phenol and 32 parts of methanol (molar ratio 5:1) are reacted in the presence of the strongly acidic cation exchanger described in Example 1 under the conditions described in Example 2.

The resulting reaction mixture consists of: 442.7 parts of phenol, 22.7 parts of methanol, 31.3 parts of anisole and 5.2 parts of water; i.e. the yield of anisole is approx. 100%, based on the reacted methanol (or phenol). The proportion of nuclear-alkylated products is below 1% by weight.

The alkylation was conducted in the same way, but instead of the strongly acidic cation exchanger used the following strongly acidic cation exchangers were employed:
(a) gel-type cation exchangers (polystyrene sulphonic acid cross-linked with 2% by weight of divinyl benzene)
(b) gel-type cation exchangers (polystyrene sulphonic acid cross-linked with 8% by weight of divinyl benzene)
(c) macroporous cation exchangers (polystyrene sulphonic acid cross-linked with 8% by weight of divinyl benzene, the matrix of which was made macroporous with 37% by weight of isododecane)
(d) macroporous cation exchangers (polystyrene sulphonic acid cross-linked with 18% by weight of divinyl benzene, the matrix of which was made macroporous with 40% by weight of isododecane).

With all the cation exchangers anisole yields of practically 100%, based on the reacted methanol (or phenol), were obtained. The proportion of nuclear-alkylated compounds was also below 0.3% by weight in all the tests. Only the reaction rates and thus the conversion rates per unit of time varied. The rate of the reaction as a percentage of that achieved with the catalyst described in Example 1 was 95% using cation exchanger a), 70% using cation exchanger b), 60% using cation exchanger c) and 60% using cation exchanger d).

EXAMPLE 9

541 parts of m-cresol, 32 parts of methanol and 86 parts (15% by weight) of the strongly acidic dry cation exchanger described in Example 1 are reacted for 25 hours under the reaction conditions described in Example 2.

The resulting reaction mixture consists of: 519.4 parts of m-cresol, 24.4 parts of m-cresylmethyl ether, 25.6 parts of methanol and 3.6 parts of water; i.e. the yield of m-cresylmethyl ether is 100% based on the reacted methanol (or m-cresol). The proportion of nuclear-alkylated compounds is below 0.1% by weight.

EXAMPLE 10

720 parts of β-naphthol, 32 parts of methanol and 190 parts (25% by weight) of the strongly acidic dry cation exchanger described in Example 1 are reacted for 15 hours under the reaction conditions described in Example 2.

The resulting reaction mixture consists of: 583.2 parts of β-naphthol, 150.1 parts of β-naphthyl methyl ether, 1.6 parts of methanol and 17.1 parts of water; i.e. the yield of β-naphthyl methyl ether is 100%, based on the reacted methanol (or β-naphthol). The proportion of nuclear-alkylated compounds is below 0.1% by weight.

EXAMPLE 11

550 parts of hydroquinone, 16 parts of methanol and 113 parts (20% by weight) of the strongly acidic, dry cation exchanger described in Example 1 are reacted in 500 ml of 1,4-dioxane and under the reaction conditions described in Example 2.

The resulting reaction mixture consists of (after the dioxane has been drawn off): 517.6 parts of hydroquinone, 96.6 parts of hydroquinone monomethyl ether, 6.4 parts of methanol and 5.4 parts of water; i.e. the yield of hydroquinone monomethyl ether is 100%, based on the reacted methanol (or hydroquinone). The proportion of nuclear-alkylated compounds is below 0.1% by weight, the proportion of hydroquinone dimethyl ether is below 0.1% by weight.

What is claimed is:

1. In the known process for the preparation of alkyl aryl ethers by reacting aromatic hydroxy compounds with aliphatic alcohols in the presence of strongly acidic cation exchangers based on synthetic resins the improvement comprising using at least 3 moles of aromatic hydroxy compound per mol of aliphatic alcohol.

2. The process according to claim 1, wherein the molar ratio of aromatic hydroxy compound to aliphatic alcohol is 3–5:1.

3. The process according to claim 1, wherein a gel-type polystyrene sulphonic acid cross-linked with 2 to 4% by weight of divinyl benzene is used as strongly acidic cation exchanger.

4. The process according to claim 1, wherein the reactants consist essentially of the aromatic hydroxy compound and the aliphatic alcohol.

5. The process according to claim 1, wherein the aliphatic alcohol is selected from the group consisting of methanol, ethanol, propanol, butanol, isobutanol, pentanol, isopentanol, hexanol, isohexanol, heptanol, isoheptanol, octanol and isooctanol.

6. The process according to claim 5, wherein the reactants consist essentially of the aromatic hydroxy compound and the aliphatic alcohol, the molar ratio of aromatic hydroxy compound to aliphatic alcohol is 3–5:1, and a gel-type polystyrene sulphonic acid cross-linked with 2 to 4% by weight of divinyl benzene is used as strongly acidic cation exchanger.

* * * * *